United States Patent [19]

Spencer

[11] Patent Number: 5,364,777
[45] Date of Patent: Nov. 15, 1994

[54] METHOD OF IMPROVING LIPASE ACTIVITY USING NOBLE GASES

[75] Inventor: Kevin C. Spencer, Hinsdale, Ill.

[73] Assignee: American Air Liquide, Walnut Creek, Calif.

[21] Appl. No.: 862,726

[22] Filed: Apr. 3, 1992

[51] Int. Cl.$^5$ .......................... C12P 7/64; C12N 9/99; C12N 9/88

[52] U.S. Cl. .................................. 435/134; 435/183; 435/184; 435/189; 435/193; 435/195; 435/232; 435/233; 435/262; 423/262

[58] Field of Search ............... 435/134, 183, 184, 189, 435/193, 195, 232, 233; 423/262

[56] References Cited

U.S. PATENT DOCUMENTS

| | | | |
|---|---|---|---|
| 2,569,217 | 9/1951 | Bagdigian | 426/413 |
| 3,143,471 | 8/1964 | Coady | 167/78 |
| 3,183,171 | 5/1965 | Schreiner | 200/18 |
| 3,378,443 | 4/1968 | Cooper et al. | 167/78 |
| 3,677,024 | 7/1972 | Segall | 62/64 |
| 3,725,076 | 4/1973 | Stefanucci et al. | 426/393 |
| 3,957,892 | 5/1976 | Kleiman | 260/652.5 |
| 4,008,754 | 2/1977 | Kraushaar et al. | 165/2 |
| 4,017,363 | 4/1977 | McMullen et al. | 435/96 |
| 4,044,004 | 8/1977 | Saucy et al. | 260/345.3 |
| 4,136,049 | 1/1979 | Horiishi et al. | 252/62.56 |
| 4,138,565 | 2/1979 | Ehrhardt et al. | 544/346 |
| 4,308,264 | 12/1981 | Conway et al. | 424/236 |
| 4,314,810 | 2/1982 | Fourcadier et al. | 8/410 |
| 4,315,266 | 2/1982 | Ellis, Jr. | 343/895 |
| 4,450,960 | 5/1984 | Johnson | 206/334 |
| 4,496,397 | 1/1985 | Waite | 106/161 |
| 4,501,814 | 2/1985 | Schoenrock et al. | 435/94 |
| 4,548,605 | 10/1985 | Iwamoto et al. | 604/410 |
| 4,622,425 | 11/1986 | Gagne | 562/595 |
| 4,664,256 | 5/1987 | Halskov | 264/55 |
| 4,812,320 | 3/1989 | Ruzek | 426/393 |
| 4,830,858 | 3/1989 | Payne et al. | 424/450 |
| 4,892,579 | 1/1990 | Hazelton | 75/0.5 BB |
| 4,895,726 | 1/1990 | Curtet et al. | 424/456 |
| 4,895,729 | 1/1990 | Powrie et al. | 426/316 |
| 4,919,955 | 4/1990 | Mitchell | 426/394 |
| 4,946,326 | 8/1990 | Schvester et al. | 426/316 |
| 4,965,165 | 10/1990 | Saccocio et al. | 430/138 |
| 4,971,813 | 11/1990 | Strobel et al. | 426/51 |
| 5,004,623 | 4/1991 | Giddy et al. | 426/564 |
| 5,006,222 | 4/1991 | Sequeria, Jr. | 208/33 |
| 5,021,251 | 6/1991 | McKenna et al. | 426/599 |
| 5,030,778 | 7/1991 | Ransford | 570/208 |
| 5,045,529 | 9/1991 | Chiang | 514/6 |
| 5,064,070 | 11/1991 | Higashiyama | 206/455 |
| 5,108,656 | 4/1992 | Schvester et al. | 252/380 |
| 5,128,160 | 7/1992 | Fath et al. | 426/316 |

FOREIGN PATENT DOCUMENTS

| | | |
|---|---|---|
| 989311 | 5/1976 | Canada . |
| 204532 | of 0000 | European Pat. Off. . |
| 0111595 | 6/1984 | European Pat. Off. . |
| 0346201 | 12/1989 | European Pat. Off. . |
| 0412155 | 2/1991 | European Pat. Off. . |
| 0440273 | 8/1991 | European Pat. Off. . |
| 2156559 | 6/1973 | France . |
| 2225095 | 11/1974 | France . |
| 2261518 | 9/1975 | France . |
| 2406567 | 5/1979 | France . |
| 1339669 | 9/1983 | France . |
| 1454653 | 8/1986 | France . |
| 2643232 | 8/1990 | France . |
| 0635601 | 9/1936 | Germany . |
| 3007712 | 10/1981 | Germany . |
| 52-27699 | 9/1972 | Japan . |

(List continued on next page.)

OTHER PUBLICATIONS

Colter et al. *Undersea Biomedical Research* vol. 17 (4) 1990 pp. 297–304 (see Abstract).

(List continued on next page.)

*Primary Examiner*—L. Blaine Lankford
*Attorney, Agent, or Firm*—Oblon, Spivak, McClelland, Maier & Neustadt

[57] ABSTRACT

The activity of a lipase is improved in processes where the lipase is contacted with a noble gas. The gases neon, argon, xenon, and krypton when contacted with the lipase improve the activity of the lipase when the process is performed at a pressure less than 100 atmospheres.

6 Claims, 6 Drawing Sheets

FOREIGN PATENT DOCUMENTS

| | | |
|---|---|---|
| 52-86987 | 7/1977 | Japan . |
| 52-97913 | 8/1977 | Japan . |
| 54-129185 | 10/1979 | Japan . |
| 1-059647 | 1/1980 | Japan . |
| 58-39650 | 3/1983 | Japan . |
| 58-107180 | 6/1983 | Japan . |
| 60-56984 | 4/1985 | Japan . |
| 63-77848 | 4/1988 | Japan . |
| 2-104502 | 4/1990 | Japan . |
| 3-200568 | 9/1991 | Japan . |
| 0415656 | 8/1934 | United Kingdom . |
| 1376362 | 12/1974 | United Kingdom . |
| 2029846 | 3/1980 | United Kingdom . |
| 2091556 | 8/1982 | United Kingdom . |
| 1289437 | 2/1987 | U.S.S.R. . |

OTHER PUBLICATIONS

Doebbler et al. *Fed Proc* vol. 26 1967 p. 650 (see Abstract).

Federation Proceedings, vol. 26, No. 2, Mar.–Apr. 1967, p. 650, G. F. Doebbler, et al., "Inert Gas Interactions and Effects on Enzymatically Active Proteins".

Febs Letters, vol. 62, No. 3, Mar. 1976, pp. 284–287, K. Sandoff, et al., "Effect of Xenon, Nitrous Oxide and Halothane on Membrane-Bound Sialidase From Calf Brain".

Aviation, Space and Environmental Medicine, vol. 48, No. 1, Jan. 1977, pp. 40–43, S. K. Henrick, et al., "Effect of Increased Pressures of Oxygen, Nitrogen, and Helium on Activity of A Na-K-Mg ATPase of Beef Brain".

Undersea Biomedical Research, vol. 17, No. 4, 1990, pp. 297–303, J. S. Colton, et al., "Effect of Helium and Heliox on Glutamate Decarboxylase Activity".

Sciences Des Aliments, vol. 4, 1984, pp. 595–608, B. Pichard, et al., "Effect of Nitrogen, Carbon Monoxide and Carbon Dioxyde on the Activity of Proteases of Pseudomonas Fragi and Streptomyces Caespitosus".

Chemical Abstracts, vol. 68, No. 14, AN-60751j.
Chemical Abstracts, vol. 74, No. 23, AN-121276I.
Chemical Abstracts, vol. 76, No. 12, AN-70898s.
Chemical Abstracts, vol. 80, No. 7, AN-35579z.
Chemical Abstracts, vol. 80, No. 11, AN-56112g.
Chemical Abstracts, vol. 86, No. 3, AN-14672h.
Chemical Abstracts, vol. 87, No. 22, AN-172800y.
Chemical Abstracts, vol. 91, No. 17, AN-138183x.
Chemical Abstracts, vol. 93, No. 24, AN-225670p.
Chemical Abstracts, vol. 97, No. 18, AN-145890c.
Chemical Abstracts, vol. 98, No. 10, AN-78191f.
Chemical Abstracts, vol. 99, No. 21, AN-172397v.
Chemical Abstracts, vol. 106, No. 25, AN-210601e.
Chemical Abstracts, vol. 115, No. 20, AN-214644e.
WPI Abstracts, AN-70-84762R, DE-1753586.
WPI Abstracts, AN-82-05785E, DE-3 202 622, Sep. 9, 1982.

Federation Proceedings, vol. 27, No. 3, May–Jun. 1968, H. R. Schreiner, "General Biological Effects of the Helium–Xenon Series of Elements".

156 Food Technology, vol. 34, No. 6, Jun. 1980, p. 102.

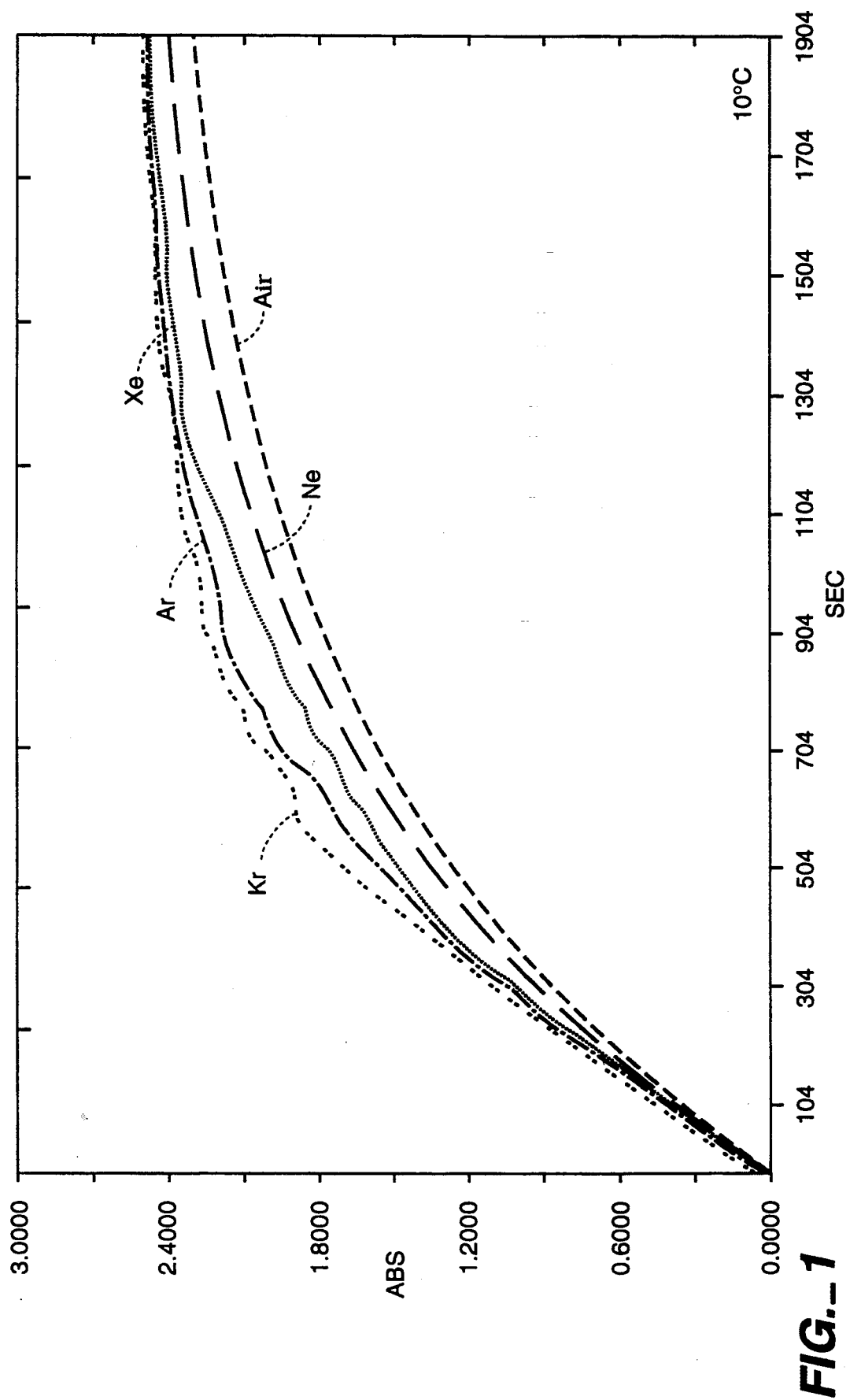
FIG._1

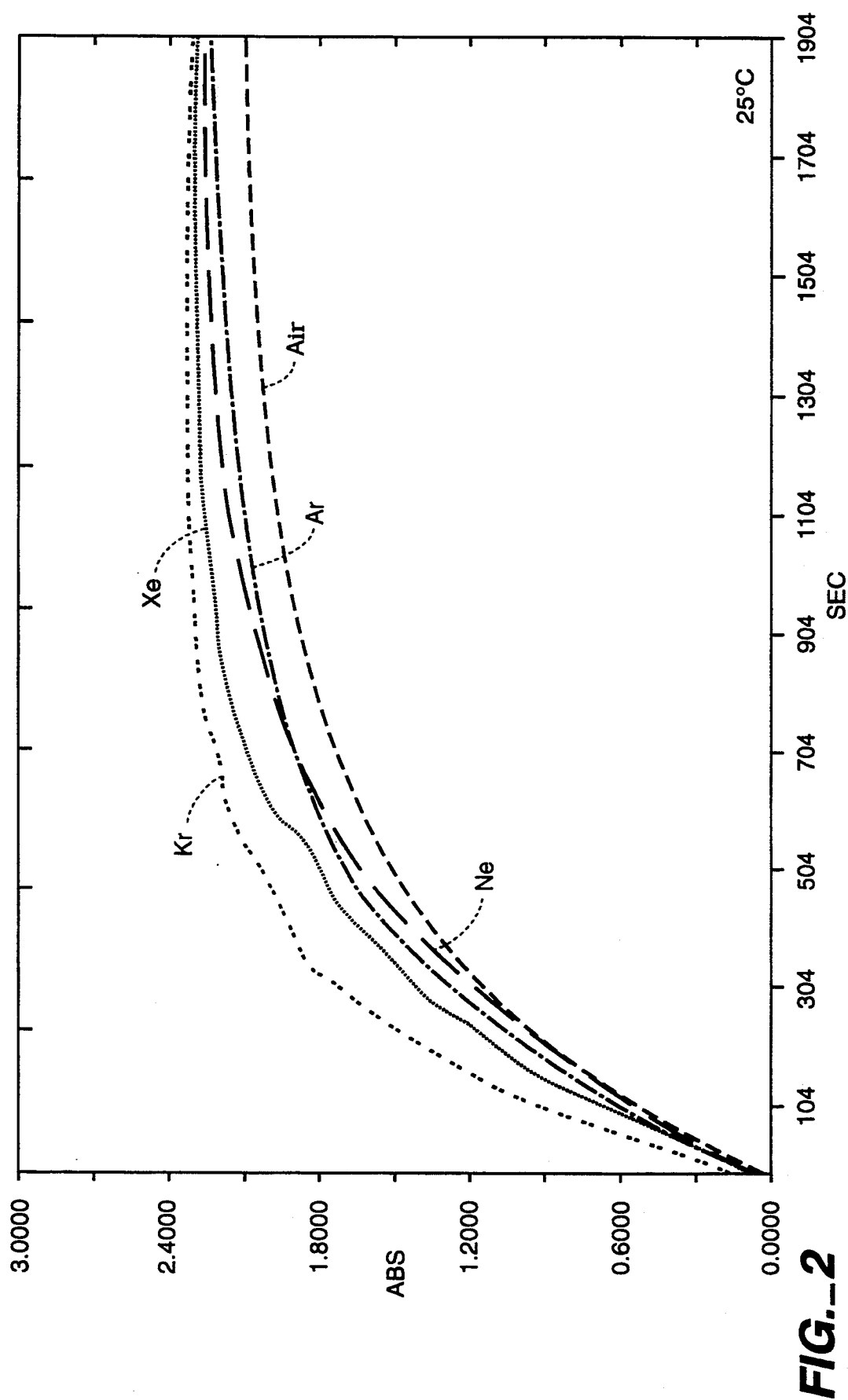
FIG._2

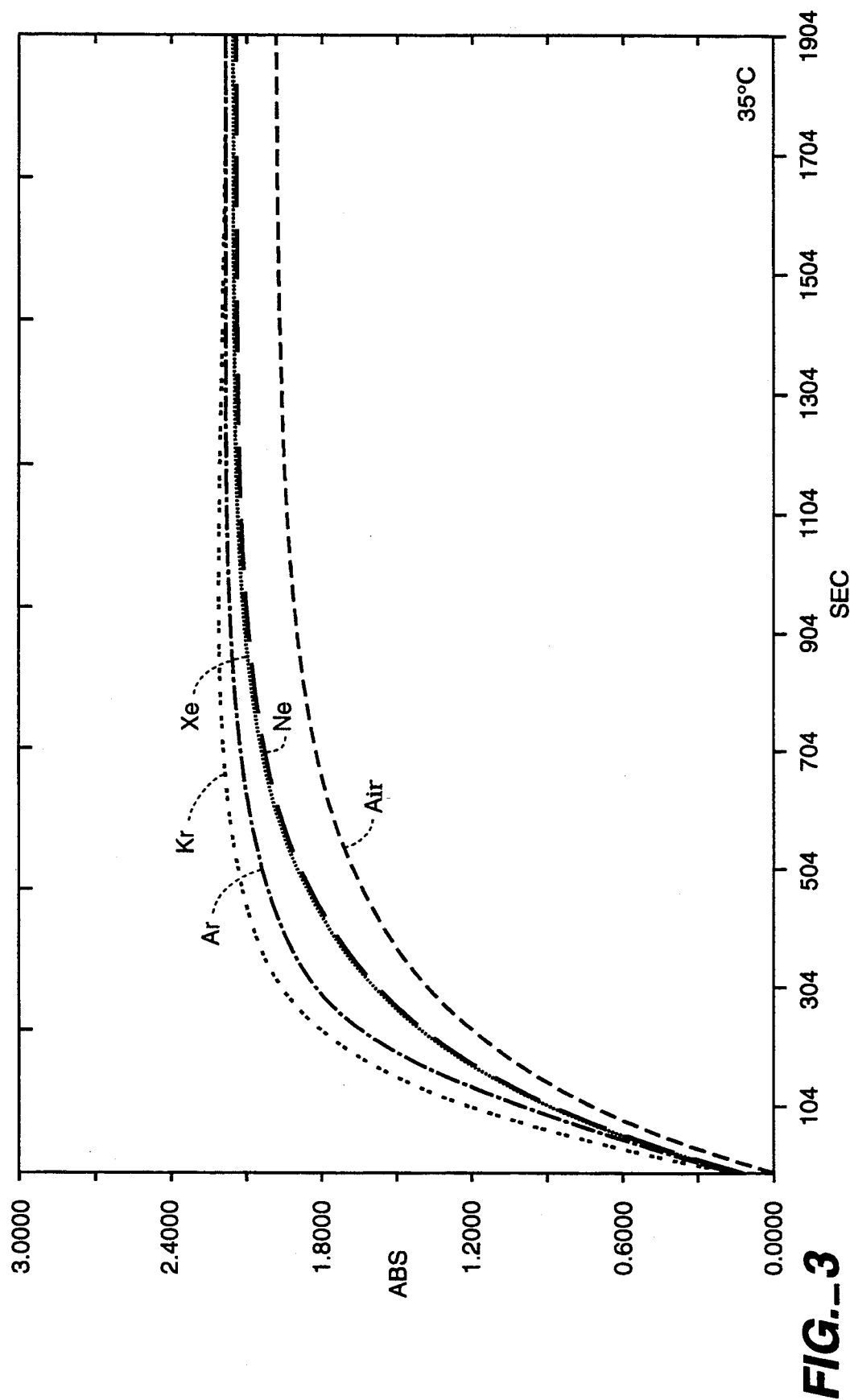
FIG._3

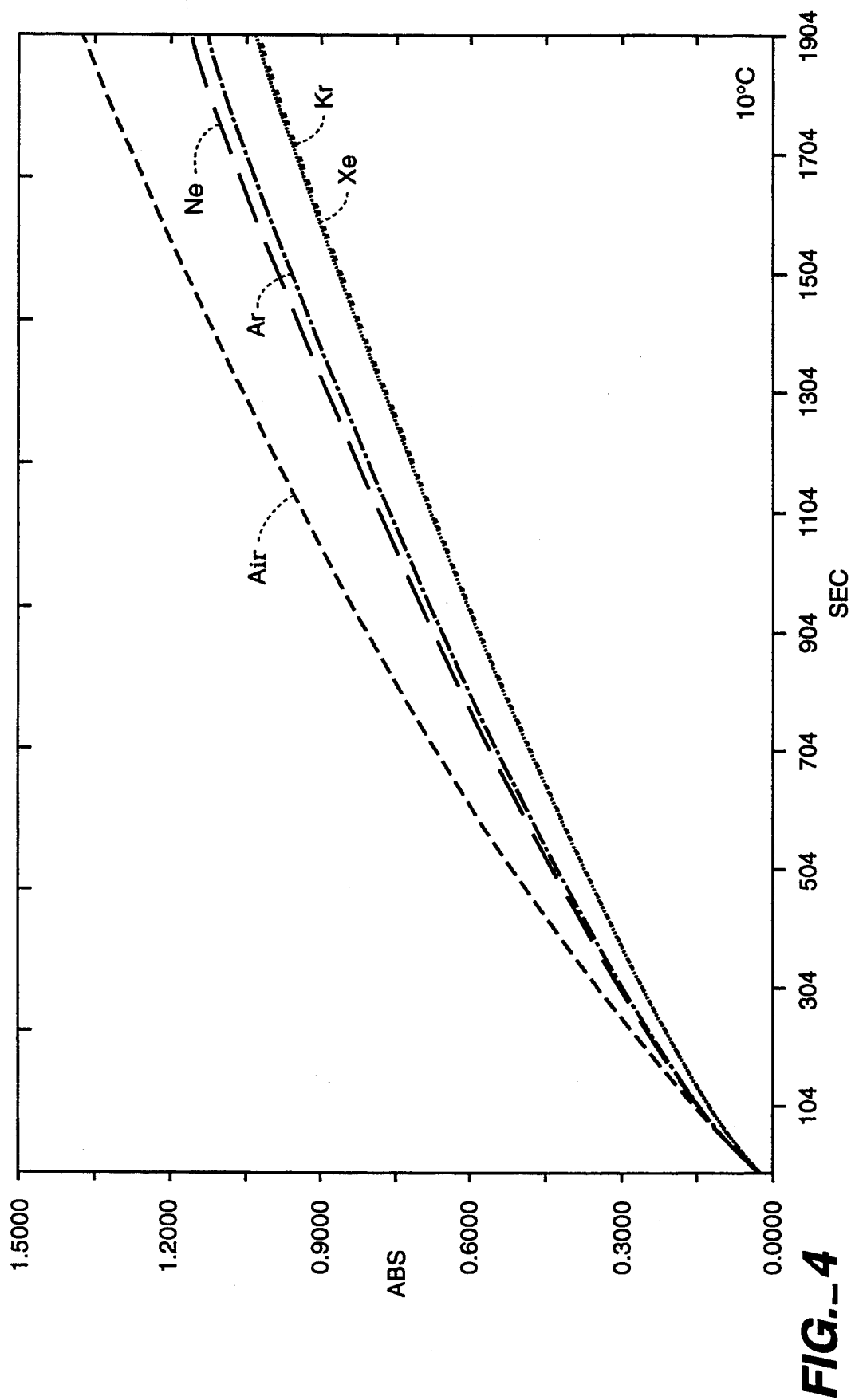
FIG._4

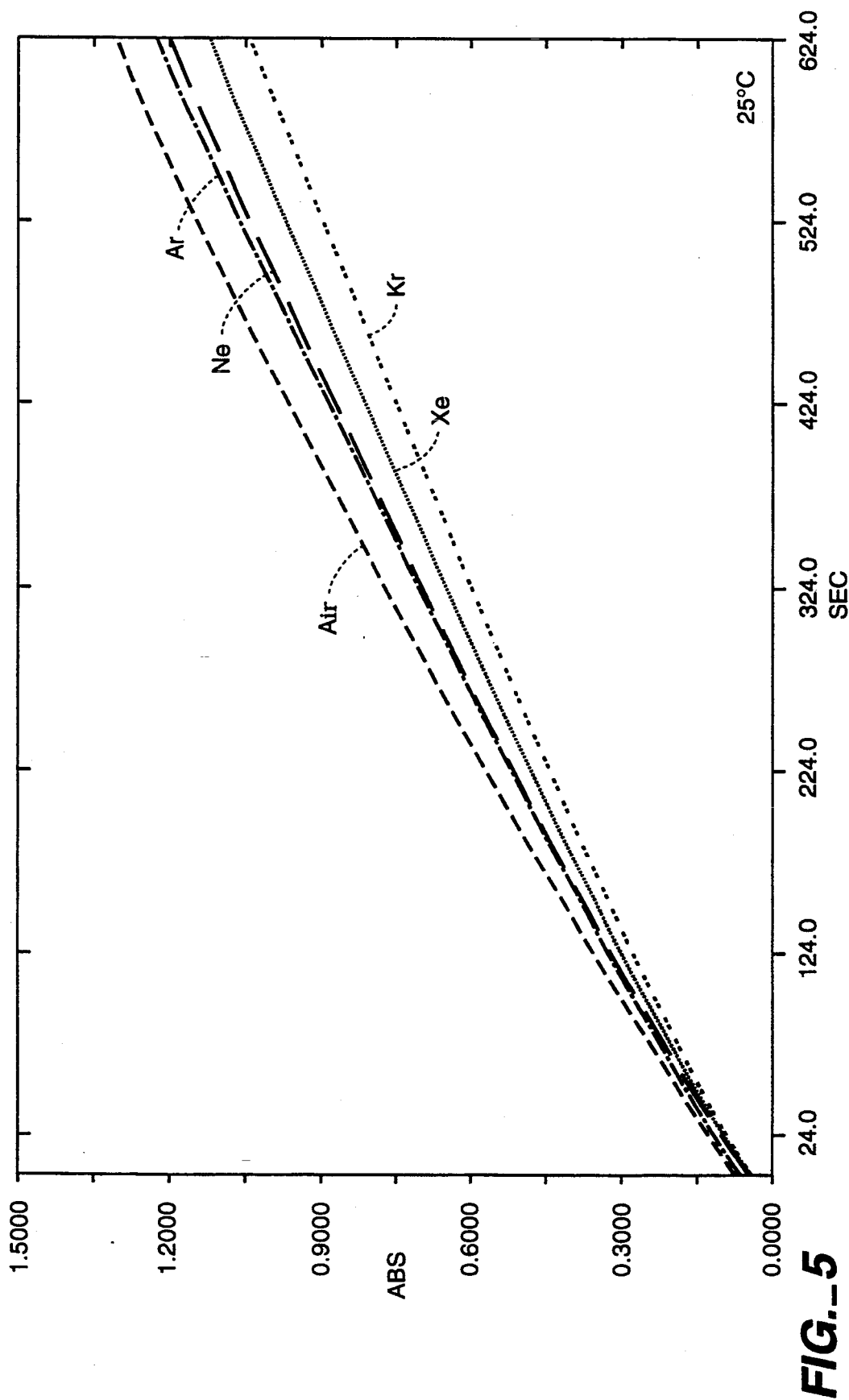
FIG._5

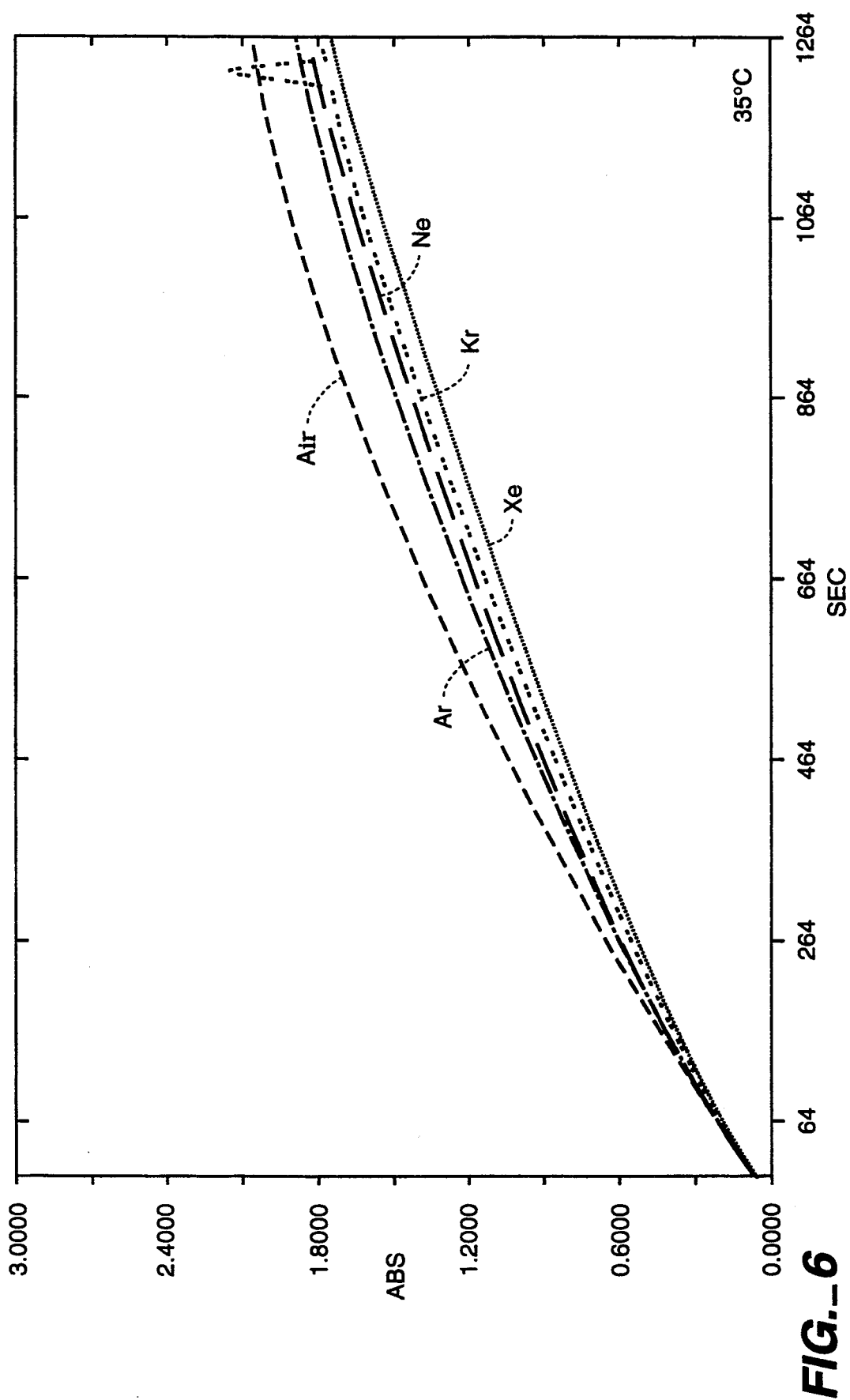
FIG._6

METHOD OF IMPROVING LIPASE ACTIVITY USING NOBLE GASES

BACKGROUND OF THE INVENTION

Field of the Invention

The present inventions relates to a method of improving enzymatic lipid processing using noble gases.

Description of the Background

Lipases are used commercially to break down triglycerides into their component diglycerides, monoglycerides, glycerol, and fatty acids. Lipases are used at each stage of this reaction sequence, and may be combined with chemical treatments to produce desired products. Commercial lipase processes include, for example, the preparation of oils and soaps, flavors and fragrances, fatty acid production, conversion of fats and oils into desired reaction products as by interesterification, production of fatty acid esters. Different lipases may be used at different steps. The lipase which is used to convert triglycerides to fatty acids is triacylglycerol acylhydrolase, which is triacylglycerol lipase EC 3.1.1.3. See *Enzymes*, Dixon Webb (Third Edition, Academic Press).

Other commercially important lipases include monoacylglycerol lipase EC 3.1.1.23, and lipoprotein lipase 3.1.1.34.

Control of lipase activity is currently limited to indirect control with chemical process methods such as control of temperature, water availability, stirring, and other nonspecific treatments. Loss of enzyme activity during the process is an important cost and control factor.

Hence, it would be extremely desirable to obtain a means for improving enzymatic lipid processing by directly controlling lipase activity.

SUMMARY OF THE INVENTION

Accordingly, it is an object of the present invention to provide a method for improving enzymatic lipid processing.

It is also an object of the present invention to provide a method for directly controlling lipase activity.

The above objects and others are provided by a method for improving enzymatic lipid processing, which entails subjecting the process to a noble gas, mixture of noble gases or mixture containing at least one noble gas during at least a portion of the processing.

BRIEF DESCRIPTION OF THE DRAWINGS

FIGS. 1-3 show a typical enzyme assay carried out at 10, 25 and 35 degrees °C. for triacylglycerol lipase catalysts of paranitrophenol acetate hydrolysis. Significant improvement in rate is demonstrated in using noble gases, the order changing with each temperature.

FIGS. 4-6 show a typical and similar enzyme assay carried out on the same enzyme using PNP-butyrate showing inhibition of activity at 10° C. 25° C. and 35° C., respectively. Significant depression in rate is noted.

DETAILED DESCRIPTION OF THE PREFERRED EMBODIMENTS

In accordance with the present invention, it has been surprisingly discovered that enzymatic lipid processing may be surprisingly improved by subjecting the process to a noble gas, mixture of noble gases or mixture containing at least an noble gas during at least a portion of the processing.

Generally, the effect of the present invention is obtained by directly controlling lipase activity through the interaction of the one or more lipase enzymes used in the process with the gases of the present invention.

As used herein, the term "noble gas" means argon, krypton, neon or xenon. Helium is not preferred due to its ease of escape, while Radon is not used as it is dangerously radioactive. Any one or mixture of argon, krypton, neon or xenon may be used.

Generally, in accordance with the present invention, control of lipase processes is surprisingly improved and the processus can be either enhanced or inhibited as needed.

For example, by contacting the lipase with a noble gas, mixture of noble gases or mixture containing at least one noble gas both the rate and yield of the lipase activity may be increased as needed. Further, the effect of the present invention may be obtained across the entire range of physical conditions currently in use in the lipid industry. Importantly, control of lipase processes is now possible.

For example, binary mixtures of gases, such as argon-xenon, krypton-xenon, and argon-neon may be used, for example in any relative mixture of from 0.01% to 99.99% by volume. However, ternary or even quaternary mixtures, such as argon-xenon-krypton, argon-neon-xenon, argon-krypton-xenon may be used with the relative ranges described above.

As a mixture of noble gases, however, it is preferred to use plant offstream of about 90:10 Kr/Xe.

As a mixture of gases containing at least one noble gas, carrier gases such as nitrogen, oxygen, nitrous oxide or carbon dioxide may be used. Helium may be both a noble or carrier gas.

Further, it is advantageous to use deoxygenated air containing one or more noble gases. As used herein, the term "deoxygenated" means having less oxygen therein than normally found in air, such as not more than 10 volume %. Generally, however, it is preferred to use air having therein not more than about 5 volume % oxygen therein.

In accordance with the present invention, the same may be practiced with a conventional lipid process utilizing one or more lipases.

Moreover, the present gases may be used at pressures of from about near-vacuum to about 100 atmospheres. However, it is generally preferred that a pressure be used of between about 0.001 to 3 atmospheres. Further, the temperatures used will generally be that of the process.

Having generally described the present invention, reference will now be made to certain examples which are provided solely for purposes of illustration and are not intended to be limitative.

EXAMPLES

Lipase catalysis of lipid conversion was tested using triglycerides, paranitrophenyl (PNP) acetate, PNP-butyrate, PNP-caprate, PNP-caprylate, PNP-caproate, olive oil, standard lipids and triglycerides, and other lipids. As nonlimiting examples of demonstration of the improvement, each of triacylglycerol lipase, monoacylglycerol lipase, and lipoprotein lipase were assayed and improvement was demonstrated in use of noble gases.

Maximum enhancements and inhibitions achieved were:

For triacylglycerol lipase/PNP-Caproate, +37% at 25° C. for Ar, +23% at +35 degrees for Xe, PNP-Acetate +11% for Kr at +25° C., PNP-Caprate +14% for Ar at 35° C., PNP-Butyrate 26% Xe, −25% Kr at 10° C., to −15% at other temperatures for the other noble gases.

Typically, enhancements are up to +40%, and inhibitions to 40% under certain conditions, and similar results are obtained in running process pilots as a maximum. More particularly, under current industrial conditions, enhancements of 15–30% are obtained, although the maximum yield is already at 97% under ideal conditions, but when limitation of equilibrium occurs during the process, enhancements of process equilibrium of up to 15% are also obtained under operational conditions.

Chemical stability, pH stability, and half-life of immobilized lipase were also all increased by up to 15% when immobilized lipase columns were employed.

Testing Of An Adequate Procedure
To Follow Lipase L-1754/p-Nitrophenyl
Acetate N-8130
PROTOCOL 7/19/91, 7/22/91

PURPOSE: Effect of Air, Ne, Ar, Kr, Xe, $N_2$ and $O_2$ on Lipase L-1754 using p-nitrophenyl acetate N-8130 reaction at 10° C., 25° C. and 35° C. (one substrate concentration).

ENZYME: Lipase (Sigma No. L-4384)
E.C. 3.1.1.3
Type XI from *Rhizonus arrhizus*
Lot No. 88F-0208
Unit Definition: one unit will hydrolyze 1.0 microequivalents of fatty acids from triglycerides in one hour at ph 7.7 at 37° C. using olive oil.
Suspension in 3.2 M $(NH_4)_2SO_4$ solution containing 10mM potassium phosphate pH 6.
0.4 ml
12.7 mg protein/ml
405000 units/mg protein SUBSTRATE: p-Nitrophenyl acetate (Sigma No. N-8130)
Lot No. 7OH5012
F.W. 181.1

DILUENTS: Methanol, ACS Reagent grade (UV grade)
0.01 M sodium phosphate buffer, pH 6.0
0.05 M Trizma-Hcl buffer, pH 7.2

Solution Preparation:

7/19/91  Soln A: 0.05 M Trizma-HCl buffer, pH 7.2 at 25° C.
Add 7.02 g Trizma-HCl to 0.67 g Trizma-Base and dilute to 1 L.
pH tested: 7.05 at 25° C.

7/19/91  Soln B: 0.01 M sodium phosphate buffer, pH 6.0 at 25° C.
(x): 0.1420 9 $Na_2HPO_4$ diluted to 1 L
(y): 0.1200 g $NaH_2PO_4$ diluted to 1 L
Add 40 mi (x) to 460 ml (y) and dilute to 1 L.
pH tested: 6.10 at 25° C.

7/22/91  Soln C: 50 mM methanolic p-Nitrophenyl acetate soln
Note: p-nitrophenyl acetate is not very soluble in water therefore it is suggested that we dissolve in MeOH.
Dissolve 0.2264 g p-nitrophenyl acetate N-8130 in 25 ml Methanol (uv grade). Store in an amber bottle, keep refrigerated when not in use.

7/22/91  Soln D: p-nitrophenyl acetate in Soln C (pH 6.1)
Add 1 ml methanolic nitrophenyl acetate (Soln C) to 99 ml 0.01 M sodium phosphate buffer pH 6.1 (Soln B).

7/22/91  Soln E: Lipase L-4384 soln (3609 units/ml) Transfer the entire 0.4 ml vial with 57 ml Soln A to an amber bottle. Invert to mix. Refrigerate.

PARAMETERS:
GASEOUS ATMOSPHERES:
8 DIFFERENT GASEOUS ATMOSPHERES:
->G1 Air
G2 Ne
G3 Ar
G4 Kr
G5 Xe
->G6 Air
G7 $O_2$
G8 $N_2$
TEMPERATURES:
3 DIFFERENT TEMPERATURES:
T1 10° C.
T2 25° C.
T3 35° C.

-continued

BLANK:
The blank should be changed before each temperature.
R = 2.0 ml Soln D + 0.5 ml Soln A Sample Preparation and runs schedule:
use blue silicone
label silicone-sealed cuvettes (L3SIT?G?)
fill the cuvettes with 2.0 ml of (p-nitrophenyl acetate) soln D with a 1 cc syringe.
Fill 8 serum vials with 5.0 ml of (lipase L-4384) soln E. Stopper and crimp to effect a gas tight system.
Keep cuvettes and serum vials stoppered when they are not being gassed.

===> NEEDED:
Cuvettes with blue silicone: 8x3 (GxT)
3 (blk)
―――――
27 cuvettes tot.
Serum vials (10cc): 8 (w/ 5 ml SoLn E)
Needles: B-D 20G1 1/2

Spectrophotometric study, 25° C.
PARAM: Abs
Slit 1 nm
Speed 1500 nm/min
ASave Y
APrint N
BACKGROUND CORRECTION: 900–190 nm T1 RUNS (10° C.)
CPRG: 5 CELLS (for first 5 gases then 3 cells)
400 nm
120 pts (30 minutes)
INT 16 s
$Y_{min} = 0.0$
$Y_{max} = 2.5$ Note: spectro chamber is flushed with a continuous flow of nitrogen during the 10° C. run to prevent atmospheric moisture from condensing on the cell walls (thus affecting ABS readings).

Set digital controller on 10° C. and Fisher circulator on 5° C. and high pump speed.
Bubble 10x10cc of the appropriate gas in T1G1 ... 5 cuvettes. Refrigerate under two 10cc syringes. Keep refrigerated at least 15 minutes before running.
Bubble 10x10cc of the appropriate gas in G1 ... 5 serum vials. Refrigerate under two 10cc syringes.
Remove the cuvettes from the refrigerator and remove the syringes/needles from the cuvettes. Tap cuvettes to eliminate bubbles. Wipe walls. Put cuvettes in cell holder. Allow cuvettes to come to temperature.
Remove G1 ... 5 serum vials from fridge. Sample soln E (3600 Units/ml) with 1 cc syringes previously filled with the appropriate gas. Slide the syringes/needle through the silicone but not into the liquid layer, simultaneously push plungers into the liquid and push the plungers simultaneously, run timedrives.
([G1, G2, G3, G4, G5], T1, L3)  30 min
Bubble 10x10cc of the appropriate gas in T1G6 ... 8 cuvettes. Refrigerate under two 10cc syringes. Keep refrigerated at least 15 minutes before running.
Bubble 10x10cc of the appropriate gas in G6 ... 8 serum vials. Refrigerate under two 10cc syringes.
Remove the cuvettes from the refrigerator and remove the syringes/needles from the cuvettes. Tap cuvettes to eliminate bubbles. Wipe walls. Put cuvettes in cell holder. Allow cuvettes to come to temperature.
Remove G6 ... 8 serum vials from fridge. Sample soln E (3600 Units/ml) with 1 cc syringes previously filled with the appropriate gas. Slide the syringes/needle through the silicone but not into the liquid layer, simultaneously push plungers into the liquid and push the plungers simultaneously, run timedrives.
([G6, G7, G8], T1, L3)  30 min T2 RUNS (25° C.)
CPRG: 5 CELLS (for first 5 gases then 3 cells)
400 nm
120 pts (30 minutes)
INT 16 s
$Y_{min} = 0.0$
$Y_{max} = 2.5$ -continued Set digital controller on 25° C. and Fisher circulator
on 20° C. and high pump speed.
Bubble 10x10cc of the appropriate gas in T2G1 ... 5
cuvettes. Refrigerate under two 10cc syringes. Keep
refrigerated at least 15 minutes before running.
Bubble 5x10cc of the appropriate gas in G1 ... 5
serum vials. Refrigerate under two 10cc syringes.
Remove the cuvettes from the refrigerator and remove
the syringes/needles from the cuvettes. Tap cuvettes
to eliminate bubbles. Wipe walls. Put cuvettes in
cell holder. Allow cuvettes to come to temperature.
Remove G1 ... 5 serum vials from fridge. Sample soln
E (3600 Units/ml) with 1 cc syringes previously
filled with the appropriate gas. Slide the
syringes/needle through the silicone but not into the
liquid layer, simultaneously push plungers into the
liquid and push the plungers simultaneously, run
timedrives.
  ([G1, G2, G3, G4, G5], T2, L3)  30 min
Bubble 10x10cc of the appropriate gas in T2G6 ... 8
cuvettes. Refrigerate under two 10cc syringes. Keep
refrigerated at least 15 minutes before running.
Bubble 10x10cc of the appropriate gas in G6...8 serum
vials. Refrigerate under two 10cc syringes.
Remove the cuvettes from the refrigerator and remove
the syringes/needles from the cuvettes. Tap cuvettes
to eliminate bubbles. Wipe walls. Put cuvettes in
cell holder. Allow cuvettes to come to temperature.
Remove G6 ... 8 serum vials from fridge. Sample soln
E (3600 Units/ml) with 1 cc syringes previously
filled with the appropriate gas. Slide the
syringes/needle through the silicone but not into the
liquid layer, simultaneously push plungers into the
liquid and push the plungers simultaneously, run
timedrives.
  ([G6, G7, G8], T2, L3)  30 min T3 RUNS (35° C.)
 CPRG: 5 CELLS (for first 5 gases then 3 cells)
  400 nm 120 pts (30 minutes)
  INT 16 s
  $Y_{min} = 0.0$
  $Y_{max} = 2.5$ Set digital controller on 25° C. and Fisher circulator
on 20° C. and high pump speed.
Bubble 5x10cc of the appropriate gas in T3G1 ... 5
cuvettes. Refrigerate under two 10cc syringes. Keep
refrigerated at least 15 minutes before running.
Bubble 10x10cc of the appropriate gas in G1 ... 5
serum vials. Refrigerate under two 10cc syringes.
Remove the cuvettes from the refrigerator and remove
the syringes/needles from the cuvettes. Tap cuvettes
to eliminate bubbles. Wipe walls. Put cuvettes in
cell holder. Allow cuvettes to come to temperature.
Remove G1 ... 5 serum vials from fridge. Sample soln
E (3600 Units/ml) with 1 cc syringes previously
filled with the appropriate gas. Slide the
syringes/needle through the silicone but not into the
liquid layer, simultaneously push plungers into the
liquid and push the plungers simultaneously,
  ([G1, G2, G3, G4, G5], T3, L3)  30 min
Bubble 10x10cc of the appropriate gas in T3G6 ... 8
cuvettes. Refrigerate under two 10cc syringes. Keep
refrigerated at least 15 minutes before running.
Bubble 10x10cc of the appropriate gas in G6 ... 8
serum vials. Refrigerate under two 10cc syringes.
Remove the cuvettes from the refrigerator and remove
the syringes/needles from the cuvettes. Tap cuvettes
to eliminate bubbles. Wipe walls. Put cuvettes in
cell holder. Allow cuvettes to come to temperature.
Remove G6... 8 serum vials from fridge. Sample soln
E (3600 Units/ml) with 1 cc syringes previously
filled with the appropriate gas. Slide the
syringes/needle through the silicone but not into the
liquid layer, simultaneously push plungers into the
liquid and push the plungers simultaneously, run
timedrives.
  ([G6, G7, G8], T3, L3)  30 min SPECTRA FILES:
 L3S2T1G1... 5.SP
 L3S2T1G6... 8.SP
 L3S2T2G1... 5.SP
 L3S2T2G6... 8.SP -continued

```
        L3S2T3G1... 5.SP = = = = >these were misnamed
                              L2S2T3G1 ... 5. SP and renamed by
                              DOS to L3S2T3G1 ... 5.SP
        L3S2T3G6....8.SP
        ———————
        24 FILES
            Testing Of An Adequate Procedure
            To Follow Lipase L-1754/p-Nitrophenyl
caprate N-0252, p-Nitrophenyl butyrate N-9876, p-Nitrophenyl
    caproate N-0502, p-Nitrophenyl caprylate N-0752
                PROTOCOL 8/2/91, 8/5/91
    Noble Gas Effects on
    Biosystems
    Filename: LIPASES3.WP
    Disk: LIPASE91
PURPOSE:  Testing protocol to follow Lipase L-17,54 using p-
          nitrophenyl caprate N-0252, p-Nitrophenyl butyrate
          N-9876, p-Nitrophenyl caproate N-0502, T)
          Nitrophenyl caprylate N-0752 as substrates.
ENZYME:   Lipase (Sigma No. L-1754)
          E.C. 3.1.1.3
          Type VII from Candida cylindracea w/ 30% lactose
          extender
          Lot No. 100HO482
          Unit Definition: one unit will hydrolyze 1.0
          microequivalents of fatty acids from triglycerides
          in one hour at pH 7.2 at 37° C. using olive oil.
          900 units/mg solid
          5 g solid
SUBSTRATE:     p-Nitrophenyl acetate (Sigma No. N-8130)
          Lot No. 7OH5012
          1 g
          p-Nitrophenyl caprate (Sigma No. N-02521)
          Lot No. 17F5003
          1 g
          p-Nitrophenyl butyrate (Sigma No. N-9876)
          Lot No. 1OH5022
          1 g
          p-Nitrophenyl caproate (Sigma No. N-0502)
          Lot No. 1OH5022
          1 g
          p-Nitrophenyl caprylate (Sigma No. N-0752)
          Lot No. 10H5020
          1 g
DILUENTS: Methanol, ACS Reagent grade (UV grade)
          0.01 M sodium phosphate buffer, pH 7.0
          0.05 M Trizma-HCl buffer, pH 7.0
SOLUTION PREPARATION:
Soln A:   0.05 M Trizma-HCl buffer, pH 7.0 at 25° C.
          Add 7.02 g Trizma-HCl to 0.67 g Trizma-Base and
          dilute to 1 Liter.
          pH tested: 7.042 at 25° C.
Soln B:   0.01 M sodium phosphate buffer, pH 7.0 at 25° C.
          Add 0.45 g $Na_2HPO_4$ to 0.25 g $NaH_2PO_4$ and dilute to
          1 Liter.
          pH tested: 6.954
Soln C:   50 mM methanolic p-Nitrophenyl acetate soln
          Dissolve 90.6 mg in 10 ml Methanol (UV grade). Store
          in an amber bottle, keep refrigerated when not in
          use.
Soln D:   50 mM methanolic p-Nitrophenyl caprate soln
          Dissolve 90.6 mg in 10 ml Methanol (UV grade). Store
          in an amber bottle, keep refrigerated when not in
          use.
Soln E:   50 mM methanolic p-Nitrophenyl butyrate soln
          Dissolve 90.6 mg in 10 ml Methanol (UV grade). Store
          in an amber bottle, keep refrigerated when not in
          use.
Soln F:   50 mM methanolic p-Nitrophenyl caproate soln
          Dissolve 90.6 mg in 10 ml Methanol (UV grade). Store
          in an amber bottle, keep refrigerated when not in
          use.
Soln G:   50 mM methanolic p-Nitrophenyl caprylate soln
          Dissolve 90.6 mg in 10 ml Methanol (UV grade). Store
          in an amber bottle, keep refrigerated when not in
          use.
Soln H:   p-nitrophenyl acetate in soln B
          add 1 ml methanolic nitrophenyl acetate to 99 ml 0.01
          M sodium phosphate buffer pH 7.0 (Soln B).
Soln I:   p-nitrophenyl caprate in soln B
          add 1 ml methanolic nitrophenyl caprate to 99 ml 0.01
          M sodium phosphate buffer pH 7.0 (Soln B).
```

-continued

| | |
|---|---|
| Soln J: | p-nitrophenyl butyrate in soln B<br>add 1 ml methanolic nitrophenyl butyrate to 99 ml<br>0.01 M sodium phosphate buffer pH 7.0 (Soln B). |
| Soln K: | p-nitrophenyl caproate in soln B<br>add 1 ml methanolic nitrophenyl caproate to 99 ml<br>0.01 M sodium phosphate buffer pH 7.0 (Soln B). |
| Soln N: | Lipase L-1754 (3600 Units/ml)<br>Dilute 25 mi Soln M to 50 ml with Soln A. |

CPRG, 400 run, 60 pts, 16 s. int., 4 cells
  S = 2.0 ml Soln I + 0.5 mi Soln M    L4RXN6.SP
  S = 2.0 mi Soln J + 0.5 mi Soln M    L4RXN7.SP
  S = 2.0 ml Soln K + 0.5 mi Soln M    L4RXNS.SP
  S = 2.0 mi Soln L + 0.5 mi Soln M    L4RXN9.SP
  R = 2.5 mi Soln B

| | |
|---|---|
| Results: | The reaction is still to rapid or all four<br>substrates. We need to decrease the concentration of<br>enzyme. |
| Soln O: | Lipase L-1754 (36 U/ml)<br>Dilute 0.5 ml Soln N to 50 mi with Soln A. |
| Soln P: | Lipase L-1754 (72 U/ml)<br>Dilute 1.0 ml Soln N to 50 ml with Soln A. |
| Soln Q: | Lipase L-1754 (36 U/ml)<br>Dilute 5 ml Soln N to 50 mi with Soln A. |
| Soln R: | Lipase L-1754 (72 U/ml)<br>Dilute 20 ml Soln N to 40 mi with Soln A. |

CPRG, 400 run, 60 pts, 16 s. int., 4 cells
  S = 2.0 ml Soln I + 0.5 ml Soln    L4RXN10.SP
  S = 2.0 ml Soln J + 0.5 ml Soln    L4RXN11.SP
  S = 2.0 ml Soln K + 0.5 ml Soln    L4RXN12.SP
  S = 2.0 ml Soln L + 0.5 ml Soln    L4RXN13.SP
  R = 2.5 ml Soln B

| | |
|---|---|
| Results: | The reaction is still to rapid for all four<br>substrates. We need to decrease the concentration of<br>enzyme. |

CPRG, 400 run, 60 pts, 16 s. int., 4 cells
  S = 2.0 ml Soln I + 0.5 ml Soln O    L4RXN14.SP
  S = 2.0 ml Soln J + 0.5 ml Soln R    L4RXN15.SP
  S = 2.0 ml Soln K + 0.5 ml Soln R    L4RXN16.SP
  S = 2.0 mi Soln L + 0.5 ml Soln O    L4RXN17.SP
  R = 2.5 ml Soln B

| | |
|---|---|
| Results: | The reaction is still to rapid for all four<br>substrates. We will try enzyme concentrations of 90<br>U/mi and 60 U/ml for solutions J and K and 20 U/ml<br>for solutions I and L. |

Trial 1 cont. 8/5/91

| | |
|---|---|
| Soln C: | 50 mM methanolic p-Nitrophenyl acetate soln Dissolve<br>90.6m g in 10 ml Methanol (UV grade). Store in an<br>amber bottle, keep refrigerated when not in use. |
| Soln D: | 50 mM methanolic p-Nitrophenyl caprate soln<br>Dissolve 90.6m g in 10 ml Methanol (UV grade). Store<br>in an amber bottle, keep refrigerated when not in<br>use. |
| Soln E: | 50 mM methanolic p-Nitrophenyl butyrate soln Dissolve<br>90.6m g in 10 ml Methanol (UV grade). Store in an<br>amber bottle, keep refrigerated when not in use. |
| Soln F: | 50 mM methanolic p-Nitrophenyl caproate soln Dissolve<br>90.6m g in 10 mi Methanol (UV grade). Store in an<br>amber bottle, keep refrigerated when not in use. |
| Soln G: | 50 mM methanolic p-Nitrophenyl caprylate soln<br>Dissolve 90.6m g in 10 mi Methanol (UV grade). Store<br>in an amber bottle, keep refrigerated when not in<br>use. |
| Soln H: | p-nitrophenyl acetate in soln B<br>add 1 ml methanolic nitrophenyl acetate to 99 ml 0.01<br>M sodium phosphate buffer pH 7.0 (Soln B). |
| Soln I: | p-nitrophenyl caprate in soln B<br>add 1 ml methanolic nitrophenyl caprate to 99 ml 0.01<br>M sodium phosphate buffer pH 7.0 (Soln B). |
| Soln J: | p-nitrophenyl butyrate in soln B<br>add 1 ml methanolic nitrophenyl butyrate to 99 ml<br>0.01 M sodium phosphate buffer pH 7.0 (Soln B). |
| Soln K: | p-nitrophenyl caproate in soln B<br>add 1 mi methanolic nitrophenyl caproate to 99 ml<br>0.01 M sodium phosphate buffer pH 7.0 (Soln B). |
| Soln L: | p-nitrophenyl caprylate in soln B<br>add 1 ml methanolic nitrophenyl caprylate to 99 ml<br>0.01 M sodium phosphate buffer pH 7.0 (Soln B). |
| Soln S1: | Lipase L-1754 (90 Units/ml)<br>Dissolve 10 mg Lipase L-1754 in 100 ml Soln A. Store<br>in an amber bottle, keep refrigerated when not in<br>use. |
| Soln S2: | Lipase L-1754 (60 Units/ml) |

-continued

```
              Dilute 20 ml Soln S1 to 30 ml Soln A. Store in an
              amber bottle, keep refrigerated when not in use.
Soln S3:      Lipase L-1754 (20 Units/ml)
              Dilute 10 ml Soln S1 to 45 ml Soln A. Store in an
              amber bottle, keep refrigerated when not in use.
Note:         Solutions K and L were a pale yellow which means they
              are probably contaminated.
Spectrophotometric study, 250C, 8/5/91
    CPRG, 400 run, 80 pts, 16 s. int., 4 cells
    S = 2.0 ml Soln J + 0.5 ml Soln S1     L4RXN18.SP
    S = 2.0 ml Soln J + 0.5 ml Soln S2     L4RXN19.SP
    S = 2.0 ml Soln K + 0.5 ml Soln S1     L4RXN20.SP
    S = 2.0 ml Soln K + 0.5 ml Soln S2     L4RXN21.SP
    R = 2.0 ml Soln B + 0.5 ml Soln A
CPRGr 400 run, 80 pts, 16 s. int., 2 cells
    S = 2.0 ml Soln I + 0.5 ml Soln S3     L4RXN22.SP
    S = 2.0 ml Soln L + 0.5 ml Soln S3     L4RXN23.SP
    R = 2.0 ml Soln B + 0.5 ml Soln A
Results: We will do gas runs using p-nitrophenyl caproate and
p-nitrophenyl caprate as substrates. These will be compared to
the data we obtained during the gas run using p-nitrophenyl
acetate (see LIPASEG1.WP). The following are the
concentrations and time parameters that will be used:
        p-nitrophenyl caproate N-0502
        Lipase L-1754 (60 U/ml)
        10° C.... 30 min
        25° C.... 20 min
        35° C.... 20 min
        p-nitrophenyl caprate N-0252
        Lipase L-1754 (20 U/ml)
        10° C... 30 min
        25° C.... 20 min
        35° C.... 20 min
and using Soln A (0.05 M Trizma-HCl buffer, pH 7.0) prepared on
8/2/91 and Soln B (0.01 Sodium phosphate buffer, pH 7.0)
prepared 8/5/91.
```

Notably, the mixtures of gases containing at least one noble gas may also contain some oxygen, generally up to about 20% $O_2$, preferably up to only about 10% $O_2$.

Generally, any combination of noble gases in the presence of reasonable amounts of air or gases found therein, such as nitrogen or oxygen, under any reasonable temperature or pressure, at any concentration which is greater than the concentration of noble gases naturally occurring in air will produce the desired effect of improvement.

However, the exact improvement obtained is sensitive to temperature, pH, substrate concentration and type, enzyme concentration and salt concentration.

Further, any of the lipase enzymes described in *Enzymes* by Dixon and Webb (third Edition AP) may be controlled in accordance with the present invention.

Generally, the lipase enzymes may be in any form. For example, the enzyme regulated may be in aqueous, aqueous-based or organic solutions. The enzyme may also be in other matrices, such as a gel. Also, the enzyme may be in unbound or bound form, and even in bound form in cells.

Further, the bound enzymes may be used in batch reactors, continuous-flow-stirred-tank reactors, column reactors, such as packed bed reactor, or even fluidized bed reactors.

Moreover, it is well within the skill of the artisan to utilize the present disclosure and guidelines set forth hereinabove to determine the optimal levels of pH, temperature, pressure, [E] and [S] for any particular lipase or mixed lipase system of interest.

For example, for any particular lipase, optimal conditions of pH, pressure, temperature, [E] and [S] may abe ascertained when obtaining one or more lipase enzymes by using well known reference mammals. See, for example the catalogues of the Sigma Chemical Company for 1990 and 1991, and *Enzymes*, id. Form this knowledge, the artisan can then ascertain, using the present disclosure, the optimal mixture of gases, temperature and pressure in order to obtain the desired effects of the present invention.

Thus, the present invention may be used in conjunction with commercial processes involving the breakdown of triglycerides into diglycerides, monoglycerides, glycerol and fatty acids. For example, such processes include the preparation of oils and soaps, flavors and fragrances, fatty acid production, conversation of fats and oils by interesterification and production of fatty acid esters. These processes are well known to those skilled in the art, and the present invention may be otherwise used in conjunction with conventional equipment and methodologies for these processes.

Having described the present invention, it will now be apparent to one of ordinary skill in the art that many changes and modifications may be made without departing from the spirit and the scope of the present invention.

What is claimed as new and desired to be secured by Letters Patent of the United States is:

1. A method of using a lipase to act on a lipid substrate wherein the lipase activity is improved, which method comprises contacting at least one lipase with a lipid substrate and during at least part of said contacting, contacting said lipase at a pressure up to about 100 atmospheres with an amount effective to improve lipase activity of a gas consisting essentially of a noble gas selected from the group consisting of argon, neon, xenon, krypton and mixtures thereof.

2. The method of claim 1, wherein said gas is a mixture of said noble gases.

3. The method of claim 2, wherein said mixture of noble gases is about 90 volume % of Kr and about 10 volume % of Xe.

4. The method of claim 1, wherein said lipase is an isolated lipase.

5. The method of claim 1, wherein said lipase is in solution, in immobilized form, in a dispersion or in an organic matrix.

6. The method of claim 1, wherein said pressure is from about 0.001 to about 3 atmospheres.

* * * * *